United States Patent [19]
Lloyd

[11] Patent Number: 5,738,826
[45] Date of Patent: Apr. 14, 1998

[54] USSING CHAMBER

[76] Inventor: Mary Beth Lloyd, 455 Western Ave., Morristown, N.J. 07960

[21] Appl. No.: 694,392

[22] Filed: Aug. 12, 1996

[51] Int. Cl.$^6$ .................. B01L 3/00; G01N 15/08
[52] U.S. Cl. .................. 422/102; 73/38; 73/64.47; 422/82.02; 435/287.1; 435/288.5
[58] Field of Search .................. 422/82.01, 87.02, 422/101, 102; 73/38, 64.47; 210/321.72, 321.75, 644, 649; 435/287.1, 288.3, 288.5

[56] References Cited

U.S. PATENT DOCUMENTS 4,317,726  3/1982  Shepel .................. 422/101

OTHER PUBLICATIONS

Dharmsathaphorn et al., Am. J. Physics 246 (Gastrointest. Liver Physiol. 9), pp. G204–G208, 1984.
Schoenwald et al., J. Pharm. Sci., 72(11), pp. 1266–1272 (1983).
Precision Instrument Design, "Single Unit Diffusion Chambers," pp. 1–4, Aug. 1992.
Ussing et.al.; Dec. 23, 1950; Active Transport of Sodium As the Source of Electric Current in the Short–Circuited Isolated Frog Skin; Acta Phys., Scandinav.; vol. 23; pp. 111–127.
Field, et.al.; May 1971; Ion Transport in Rabbit Ileal Musoca I. Na and Cl Fluxes and Short–Circuit Current; Am. Jrnl. Phsiol vol. 220; No. 5; pp. 1388–1396.
Powell, et. al.; Sep. 1972; Electrolyte Secretion By the Guinea Pig Ileum In Vitro; Am. Jrnl Physiol.; vol. 223; No. 3; pp. 531–537.
Rohde, et. al.; Oct. 1973; In Vitro Measurement of Ion Fluxes Across Biopsies of Human Jejunal Mucosa During Cholera; Jrnl Applied Physiol; vol. 35; No. 4; pp. 557–561.
Powell, et.al.; Jun. 1979; Aspirin–Stimulated Intestinal Electrolyte Transport in Rabbit Ileum In Vitro; Gastroenterology; vo. 76; No. 6; pp. 1429–1437.
Berschneider, et.al; Jan. 1988; Altered Intestinal Chloride Transport In Cystic Fibrosis; FASEB J.; 2:2625–2629.

Primary Examiner—Jan Ludlow
Attorney, Agent, or Firm—Ralph T. Lilore, Esq.

[57] ABSTRACT

An apparatus which is in the nature of an Ussing chamber utilizing a discrete separation between the two chambers in which solutions used for testing tissue are located is described. The cartridge is adapted to receive small portions of the skin or tissue and is also adapted to expose each of the two surfaces of the tissue to the solution circulating in the chamber facing the tissue surface. The tissue holder is split into two halves and has holes in fluid communication with the fluid in the chamber facing the hole. The holder accommodates the tissue to be tested and when assembled and placed between the two chambers constitutes a liquid seal to maintain the liquids in each chamber separated. Ions can transfer from the tissue into each chamber depending upon the characteristics of the tissue and the nature of the solutions. The two halves of the chamber are slidably mounted on supports thus permitting the movement of the chambers away from one another further permitting the insertion or removal of the tissue holder.

7 Claims, 2 Drawing Sheets

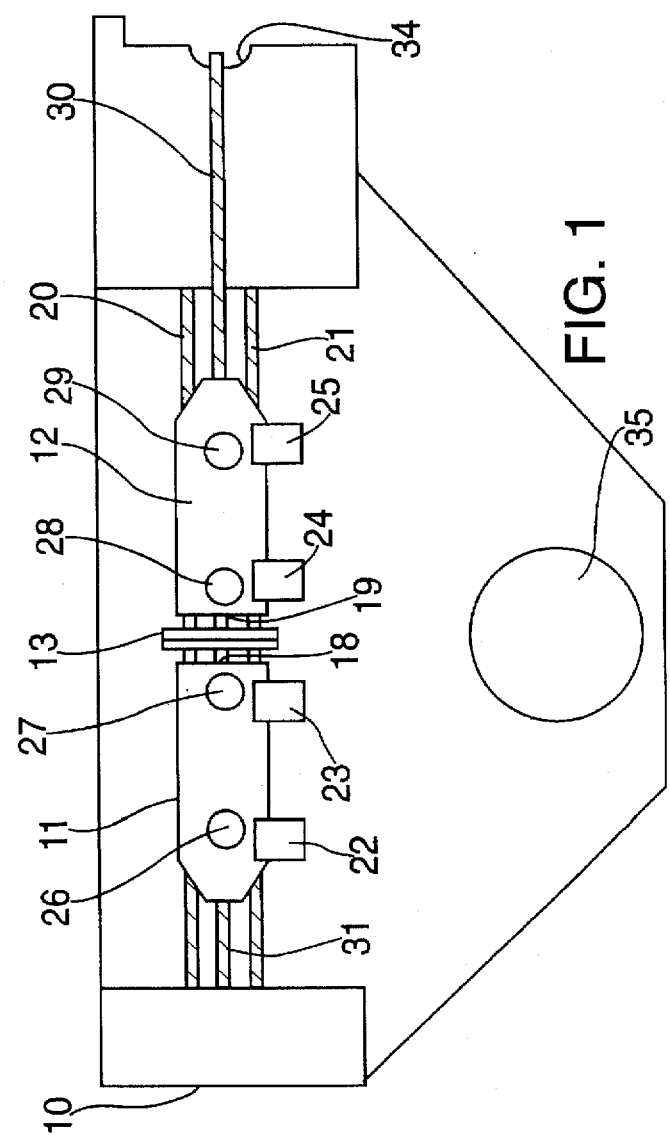
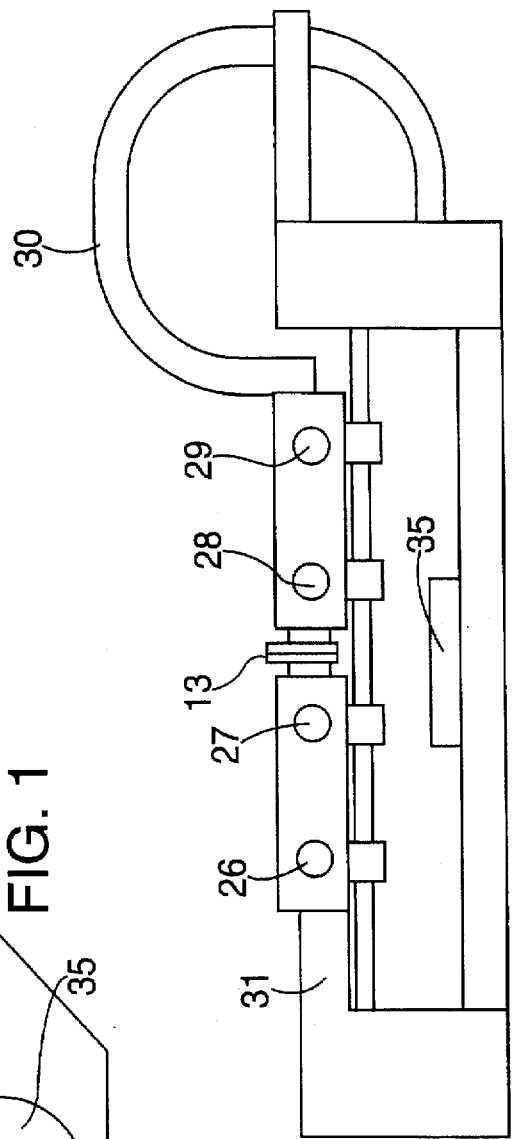
FIG. 1
FIG. 2

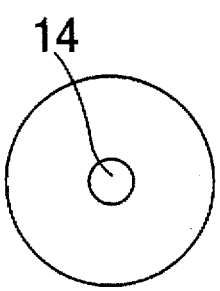
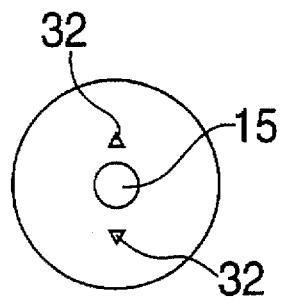
FIG. 3a   FIG. 3b
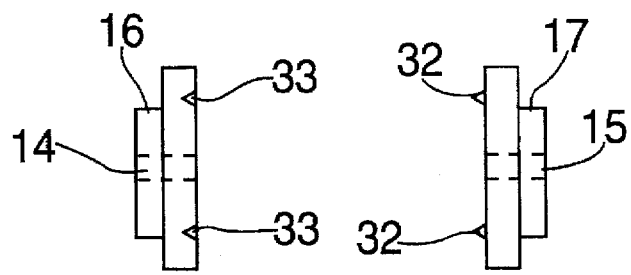
FIG. 3c   FIG. 3d
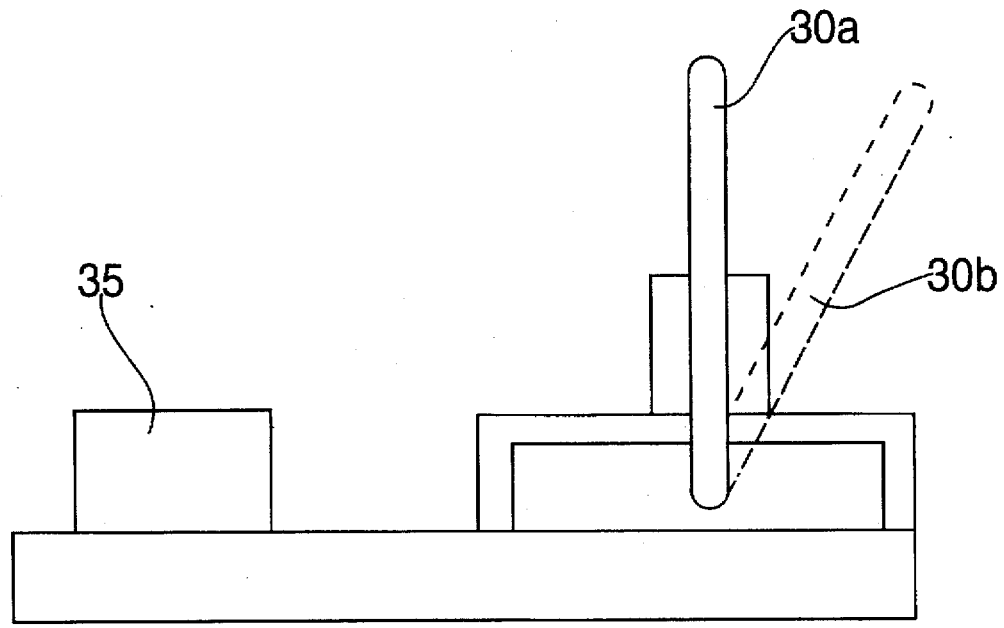
FIG. 4

USSING CHAMBER

This invention relates to an improvement in an Ussing chamber. More specifically, it relates to an improvement which renders an Ussing chamber reusable and provides a disposable cartridge for carrying the skin to be tested in an Ussing chamber.

It also provides a small, convenient, easy to produce device which facilitates the measurements normally produced in an Ussing chamber and makes available a small inexpensive unit to be disseminated widely amongst potential users. The unit permits Ussing chamber measurements to be taken rapidly with minimal downtime and with a reusable chamber of small dimensions to permit the utilization of small fragments of skin to detect potential properties of skin to salt solution permeability.

BACKGROUND
PRIOR ART

In the field of making determinations of electromotive potential across a skin membrane, it is well known to use what has come to be known as an Ussing chamber. In this chamber, there is actually a dual chamber system in which solutions may be located on either side of a sample of skin to be tested. Oftentimes in the medical and biological fields, it is important to know the electrochemical potential across a piece of tissue, not necessarily skin, to probe its vitality and general condition. Electropotential can be used to demonstrate either diseased conditions or poorly vital tissue and the measurements and data obtained from such measurements are very significant to those skilled in the art. In addition, measurements of flow of particular ions across or through the channels in the tissue are very important information to obtain. However, in the prior art Ussing chamber in order to get a reading on the potentiometer, it is necessary to introduce a tubing with gel for conductivity.

The Ussing chamber is a very well-known apparatus, the methods of use of which and the characteristics thereof are known to those skilled in the art. It contains reservoirs or chambers solutions which can be applied on either side of the tissue to be examined while electromotive force is applied to each side of the skin. The change in concentration of the solutions and the difference in charge resulting, demonstrates whether or not there is a difference in potential across the skin on one side or the other of the chamber. The difference in potential is a function of the characteristics of the tissue and of its general health, condition of structure, and basic physiology.

In the Ussing chamber as described by Ussing and Zerahn in the article from the Laboratory of Zoo Physiology at the University of Copenhagen entitled "Active Transport of Sodium as the Source of Electric Current in the Short-Circuited Isolated Frog Skin", Acta Phys. Scandinav., volume 23, pages 110-127, the authors describe the technique for determining the current that can be drawn from totally short-circuited frog skin using an Ussing chamber and using labelled sodium as a tracer.

The art has come to recognize that the difficulty with the currently available Ussing chambers is that large amounts of skin or tissue are required and the apparatus is cumbersome in its ability to be conveniently used. For example, difficulty is often encountered in affixing the skin or tissue in a manner which permits it to be exposed to liquids on each side of the tissue.

SUMMARY OF THE INVENTION

In the present invention, we have demonstrated a small apparatus which is in the nature of an Ussing chamber, but which utilizes a unique tissue holder to provide a discrete separation between the two chambers in which the solutions are located. It is by reason of this separation of the chambers via a small tissue holder interspersed therebetween and holding the skin or tissue to be analyzed, that the benefits of the invention are obtained. The tissue holder is adapted to receive small portions of the skin or tissue and is also adapted to expose two surfaces of the sample to the separate solutions as they each circulate in their respective chambers.

In the Ussing chamber in the aforementioned Scandinavian article, the skin is inserted between the two chambers and acts as a barrier to the liquid. The skin occupies a large portion of the surface area and is held in place by stretching the skin over several pins. The two chambers are placed together over the skin and mechanically clamped.

On the other hand, in the Journal of Applied Physiology, volume 35, no. 4, October 1973, in an article by Rohde and Anderson, the use of an assembly comprising a short-circuit chamber with exposed tissue areas was described. In this chamber, the tissue is located at a small opening in the chamber per se and used to block off the liquid from the chamber. At the surface of the tissue exposed to the second half of the chamber, there is located a single molded polyvinyl chloride washer tissue mount which serves to affix the tissue to one section of the chamber and to permit the other section of the chamber to be brought closer to it with the opening for the liquid to be in registration with the exposed section of the skin to be measured. The difference between the above two chambers relative to the invention is that they present cumbersome apparatuses for presenting surfaces of the tissue to the solutions in the chambers rather than a single tissue holder which can be used to separate the two chambers and be discarded after use.

Thus, the present invention provides in a single unitary housing a tissue holder which is provided in two discrete halves each of which is adapted to be exposed to fluid. The tissue holder is split into two halves and has tissue mounting means positioned so that holes in the tissue mounting means are exposed to the fluid in the chambers facing the hole. Thus, when tissue is placed in the tissue holder, and the tissue holder placed in between the two separated chambers, the liquid in each chamber contacts the portion of the tissue exposed to that chamber. An important aspect of the invention is that the two halves of the chamber are slidably mounted on tracks thus permitting the movement of the chambers away from one another further facilitating the insertion or removal of the tissue holder. An opening in each of the chambers communicates with the tissue holder and permits fluid circulating through the chambers to contact the tissue exposed through the holes in the tissue holder.

The device is also equipped with locking means to press the chambers against the tissue holder so that there is thus formed a unitary device containing the two halves of the chamber pressing upon a tissue holder mounted in between and providing the surface of the tissue as a liquid seal between the two chambers. Liquid flowing separately in the two chambers then can be measured for the electrochemical potential or changes in concentration or flow of particular ions when a piece of test tissue is inserted resulting from transport of ions into, out of, or through the tissue into the chambers. The electrochemical potential can be measured by connecting a potentiometer to a conductor, such as gold plated electrodes, that are positioned in each chamber.

There will now be described a detailed description of the invention in conjunction with the drawings presented herein.

DETAILED DESCRIPTION OF THE INVENTION AND DESCRIPTION OF THE DRAWINGS

FIG. 1 is a schematic plan view of a device of the present invention.

FIG. 2 is a schematic elevation view of the device of FIG. 1.

FIGS. 3a)–3d) are an exploded view of the tissue holder wherein FIGS. 3a) and b) show the surfaces of each half of the tissue holder which interface with the tissue, and FIGS. 3c) and d) are side views of each half of the tissue holder in separated form.

FIG. 4 is a side view of the apparatus of FIGS. 1 and 2.

The device of the invention as typified by FIG. 1 is in the form of a unitary assembled device 10 showing an Ussing-type chamber comprising two halves, 11 and 12. Interspersed between those chambers is tissue holder 13 having holes 14 and 15 (see also FIG. 3) on each of the separate sides of the tissue holder which holes will subsequently be covered in use by the tissue to be examined. Tissue holder 13 in assembled form also has protrusions 16 and 17 adapted either to be inserted into openings 18 and 19 (not shown) in the two halves of the split chambers or to overlap therewith and thereby provide fluid communication between the fluid contained in the chamber and the tissue surface facing the chamber.

The two halves of the chambers are slidably mounted on support rods 20 and 21 which anchor the chambers to the device. The purpose of having the chambers slidably mounted is to permit them to be separated to allow thereby enough space for the tissue holder to be inserted therebetween. Other elements of the device are as may be typically found in an Ussing chamber such as electrode holders 22, 23, 24, and 25 adapted to provide electrodes therethrough to contact the solutions in each of their respective chambers. In addition, each chamber is equipped with inlet and outlet ports to allow the introduction and exit of fluid therethrough. These ports are shown as inlet ports 26 and 28 and outlet ports 27 and 29 for each of the chambers.

In the embodiment shown, there is a tissue holder table 35 which is optional, but preferred. It acts as a table upon which to place one half of the tissue holder for application of the tissue to that half prior to assembling of the tissue holder into a single piece which can then be inserted as assembled tissue holder 13 into the unitary device.

Also provided on the unitary device (see FIG. 2) is a locking means 30 which in the embodiment shown in FIG. 2 is a spring-type device which can be positioned against one end of the modified Ussing chamber of the invention and the tension of the handle used to press the nearest chamber against the tissue holder the furthest chamber held in place by a stop 31. The handle 30 is held in the locked position via indent 34. The locking handle 30 is also shown in both the locked position 30a), FIG. 4, and the open position 30b), FIG. 4. The tissue holder is comprised of two halves (see FIGS. 3a), 3b), 3c), and 3d)), preferably one of which has tissue securing means in the form of pins 32 associated with one-half of the tissue holder. As shown in FIG. 3, the tissue holder is shown in separated form without the tissue having been inserted therein, merely for purposes of illustration. Holes 14 and 15 go entirely through each section because on the inner surface of the assembled tissue holder they will have the tissue separating the two halves and holes 14 and 15 will then be in fluid communication with the fluid in their Ussing chambers, but separated by the tissue. The outside surfaces of the tissue holder are press-fit against the ends of each half of the chamber each of which has holes as described previously to allow fluid to communicate with holes 14 and 15, respectively.

Those skilled in the art will be immediately aware of the operation of the device since the normal Ussing procedure is employed. The difference between art device and that of the present invention is that a much smaller piece of tissue can be employed for evaluation in a separate tissue holder. For example, in the preferred device described herein, the holes 14 and 15 which are exposed to the fluid in the chambers can be about one-sixteenth of an inch in diameter and the tissue to be applied over to them in this particular example can be approximately seven-sixteenths of an inch or so square. The tissue holder is preferably an inch in diameter or less.

The modified device shown herein may have a chamber length of less than two inches for each half and the entire assembly itself need be no longer than seven or eight inches and no higher than about two inches.

At least one half of tissue holder 13 as noted above is also preferably supplied with anchoring means so that when the two halves of the tissue holder are placed together to press a piece of tissue therebetween, the anchoring means will hold each half in place and prevent rotation. This is shown in FIG. 3 with anchoring means 32 shown juxtaposed against the other half in registration with anchoring means receiver 33.

There has thus been described a modified Ussing chamber which permits the provision of a disposable tissue holder and the utilization of a much smaller piece of tissue than has heretofore been used. This enables the judicious use of tissue and the disposability of the tissue holder and the tissue material itself if desired. With present day concerns, the proper disposal of body materials is of great importance. The tissue holder itself is very inexpensive and can be supplied in volume and quantity with the small assembly shown.

What is claimed is:

1. In an Ussing device for testing tissue specimens, said device having two discrete compartments each of which is capable of accommodating a testing solution and each of said compartments having an opening over which a surface of the tissue test specimen may be placed, and a tissue holder for holding said tissue in place and located between and separating said discrete compartments in a liquid-sealing relationship, the improvement which comprises providing in said device a base on which at least one of said discrete compartments is slidably mounted on one or more support rods affixed to said base to thereby anchor said at least one compartment to said base and facilitate movement of the compartments into open or closed positions against said tissue holder.

2. The device of claim 1 wherein the tissue holder is comprised of two halves and said tissue is held between said halves.

3. The device of claim 2 wherein each of said discrete compartments is slidably mounted on said one or more rods to facilitate separation of the compartments and insertion of the tissue holder.

4. The device of claim 3 wherein both compartments are slidably mounted on two support rods on said base.

5. The device of claim 4 wherein the compartments are compressed together by means of a spring bias locking means.

6. The device of claim 5 wherein the tissue holder comprises tissue anchoring means.

7. The device of claim 6 wherein the tissue holder is an inch or less in diameter.

* * * * *